United States Patent [19]
Bloch et al.

[11] Patent Number: 5,549,105
[45] Date of Patent: Aug. 27, 1996

[54] SUBASSEMBLY OF NETWORK OF GAS CONDUITS AND ANESTHETIC APPARATUS COMPRISING SUCH A SUBASSEMBLY

[75] Inventors: Nicolas Bloch, Paris; Yvon Guyomard, Sannois; Michel Jounenc, Les Ulis, all of France

[73] Assignee: L'air Liquide, Societe Anonyme pour l'Etude et l'Exploitation des Procedes Georges Claude, Paris Cedex, France

[21] Appl. No.: 303,503

[22] Filed: Sep. 9, 1994

[30] Foreign Application Priority Data

Sep. 9, 1993 [FR] France ................................ 93 10702

[51] Int. Cl.$^6$ .......................................... A61M 16/00
[52] U.S. Cl. ............................. 128/203.12; 128/200.24; 128/205.13; 128/204.28; 264/267; 277/167.5; 49/483.1
[58] Field of Search ................... 264/267; 128/200.24, 128/205.13, 204.18, 204.28, 716, 718, 719, 725, 730, 203.12; 277/6, 188 R, 167.5; 49/483.1

[56] References Cited

U.S. PATENT DOCUMENTS 3,687,137  8/1972  Johnson ........................ 128/204.13

FOREIGN PATENT DOCUMENTS

| 0266964 | 5/1988 | European Pat. Off. . | |
|---|---|---|---|
| 0292615 | 11/1988 | European Pat. Off. . | |
| 944269 | 12/1963 | United Kingdom | 49/483.1 |
| 1370494 | 10/1974 | United Kingdom | 49/483.1 |

OTHER PUBLICATIONS

G. Hawley, ed., "The Condensed Chemical Dictionary", (10th ed.), Van Nostrand 1981, pp. 921–922.

Brochure, "MacGregor Steel Hatch Covers", 1952.

*Primary Examiner*—V. Millin
*Assistant Examiner*—Eric P. Raciti
*Attorney, Agent, or Firm*—Young & Thompson

[57] ABSTRACT

A subassembly constituted by a body and a cover (2), defines internally gas conduit portions ($I_i$) delimited by partitions of the body coacting with sealing strips (12) in grooves (11) of the cover (2) and formed and mounted in these grooves by injection molding. The sealing strips (12) are recessed within the grooves (11) and coact with the ends of the partitions of the body extending partially into the grooves (11). For use particularly in anesthetic apparatus.

9 Claims, 3 Drawing Sheets

5,549,105

SUBASSEMBLY OF NETWORK OF GAS CONDUITS AND ANESTHETIC APPARATUS COMPRISING SUCH A SUBASSEMBLY

FIELD OF THE INVENTION

The present invention relates to a subassembly of a network of gas conduits, of the type comprising a body defining at least two conduit portions delimited by partitions of the body and by a cover on the body and comprising sealing strips disposed in recesses of the cover and coacting with the partitions of the body.

BACKGROUND OF THE INVENTION

Such assemblies, usable in numerous fields for the distribution and circulation of gas, and particularly for anesthetic apparatus for their ease of cleaning and disinfection by simply disassembling the cover and the body, can have complicated structure according to the number of the portions of conduits, thereby multiplying the number of sealing strips. Until the present, these sealing strips have been constituted by joints, generally of trapezoidal section, cut off in length and disposed manually in recesses of the cover, which requires skilled hand labor and considerable mounting time, at the same time not permitting eliminating risk of poor sealing, particularly in the region in which the joints are closed.

SUMMARY OF THE INVENTION

The present invention has for its object to provide an improved subassembly structure whose cover is pre-equipped with sealing strips which are provided in a particularly simple, reliable and trouble free manner.

To do this, according to one characteristic of the invention, the sealing strips are formed and mounted by injection molding in the recesses of the cover. According to other characteristics of the invention:

- the sealing strips are recessed in the recesses and coact with projecting portions of the partitions of the body extending partially into the recesses in the assembled configuration of the subassembly;
- in use in an anesthetic apparatus, the subassembly defines distal portions of the inhalation and exhalation branches of the patient's circuit;
- the body comprises mounting means for bellows communicating with the inhalation branch portion and a body of adsorbent interposed within the exhalation branch portion.

The present invention also has for its object an anesthetic apparatus comprising such a subassembly mounted removably on the apparatus.

BRIEF DESCRIPTION OF THE DRAWINGS

Other characteristics and advantages of the present invention will become apparent from the following description of embodiments, given by way of illustration but in no way limiting, with respect to the accompanying drawings, in which.

DETAILED DESCRIPTION OF THE INVENTION

Figure 1:
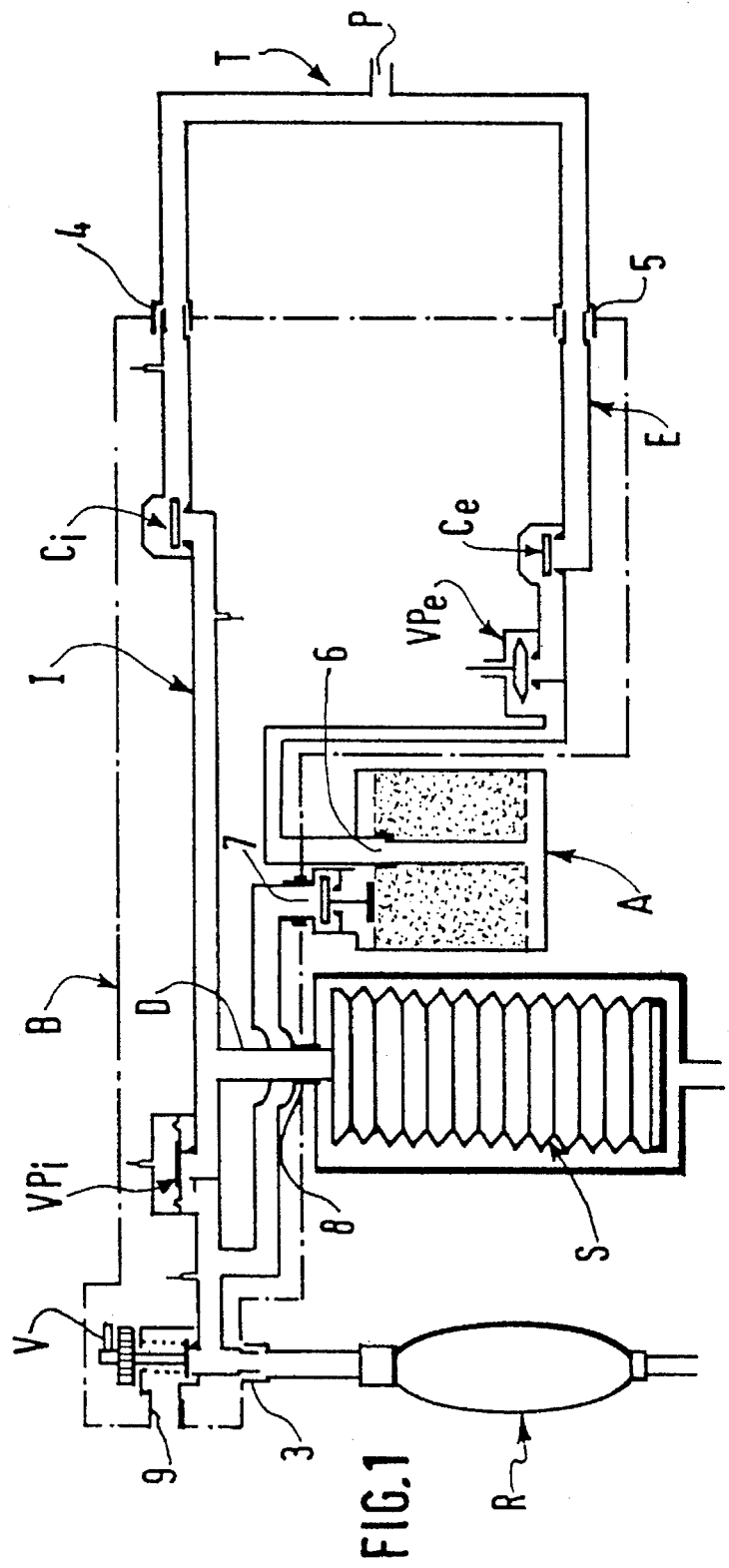
FIG. 1 is a schematic view of a closed patient circuit of an anesthetic apparatus partially constituted by a subassembly of the invention.

In FIG. 1, there will be seen the principal elements of a closed circuit patient system of an anesthetic apparatus comprising essentially an inhalation branch I, whose downstream portion is connected to tubing at T, T comprising a connection P to the respiratory passages of a patient, and an exhalation branch E whose upstream end is connected to the tubing T and whose downstream end is connected to the upstream end of the inhalation branch I into which empties, adjacent a loadable escape valve V, a circuit for the supply of makeup oxygen gas via a reservoir balloon R. The inhalation branch I comprises, upstream and downstream, a pilot valve $VD_i$ for isolation of the balloon R, a tubing D for connection to a ballasted bellows S, and a non-return valve $C_i$. The exhalation branch E comprises, in a direction upstream to downstream, a non-return valve $C_e$, a controlled exhalation valve $VP_e$ and passes through a body of absorbent A. There is shown in FIG. 1 the external contours of the subassembly B according to the invention, defining internally the indicated conduit portions and constituted by the disassemblable assembly of a body 1, of substantially flat and enclosed configuration, shown in FIG. 3, and of a cover 2, shown in FIG. 2. As will also be seen in FIG. 1, the subassembly B, in this case the body 1, comprises an inlet 3 for connection to the reservoir balloon R, an outlet 4 and an inlet 5 for connection to the tubing T, an outlet passage 6 and an inlet passage 7 for connection to the adsorbent body A, and an opening 8 for connection to the bellows S and an escape outlet 9 associated with the valve V.

Figure 3:
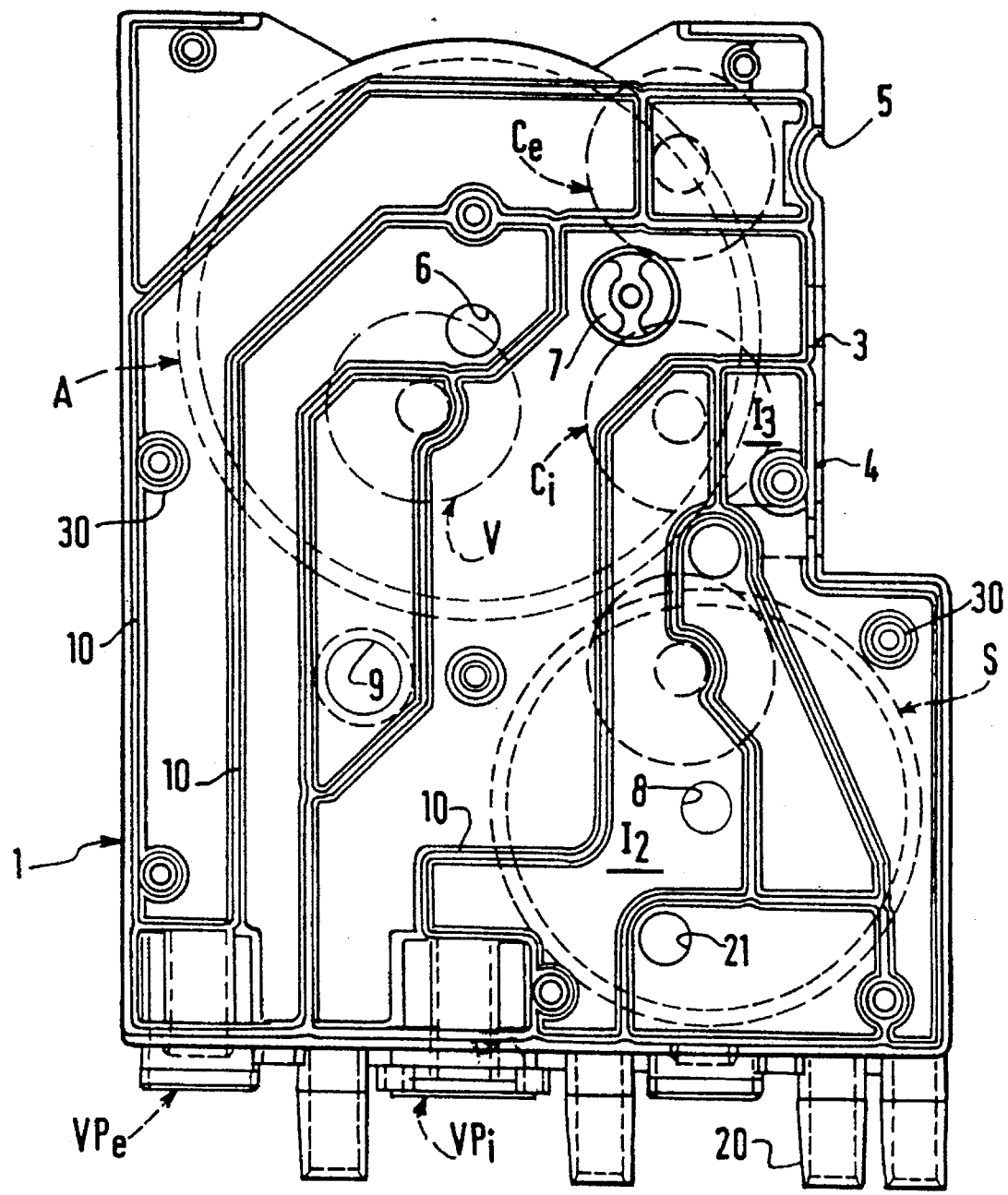

In FIG. 3 there is shown in phantom line the shape of the adsorbent body A and of the bellows envelope S which are mounted on the internal surface of the body 1, as well as the shape of the non-return valves $C_i$ and $C_e$ carried by the cover 2. As is shown in FIG. 3, the body 1, of generally parallelepipedal configuration, comprises a certain number of chambers defining the patient portions of the system of FIG. 1 and delimited laterally by partitions 10 of transverse trapezoidal profile becoming thinner in an outward direction. There are thus identified chambers $I_2$ and $I_3$ constituting the inhalation branch portion 1 in the subassembly B.

Figure 2:
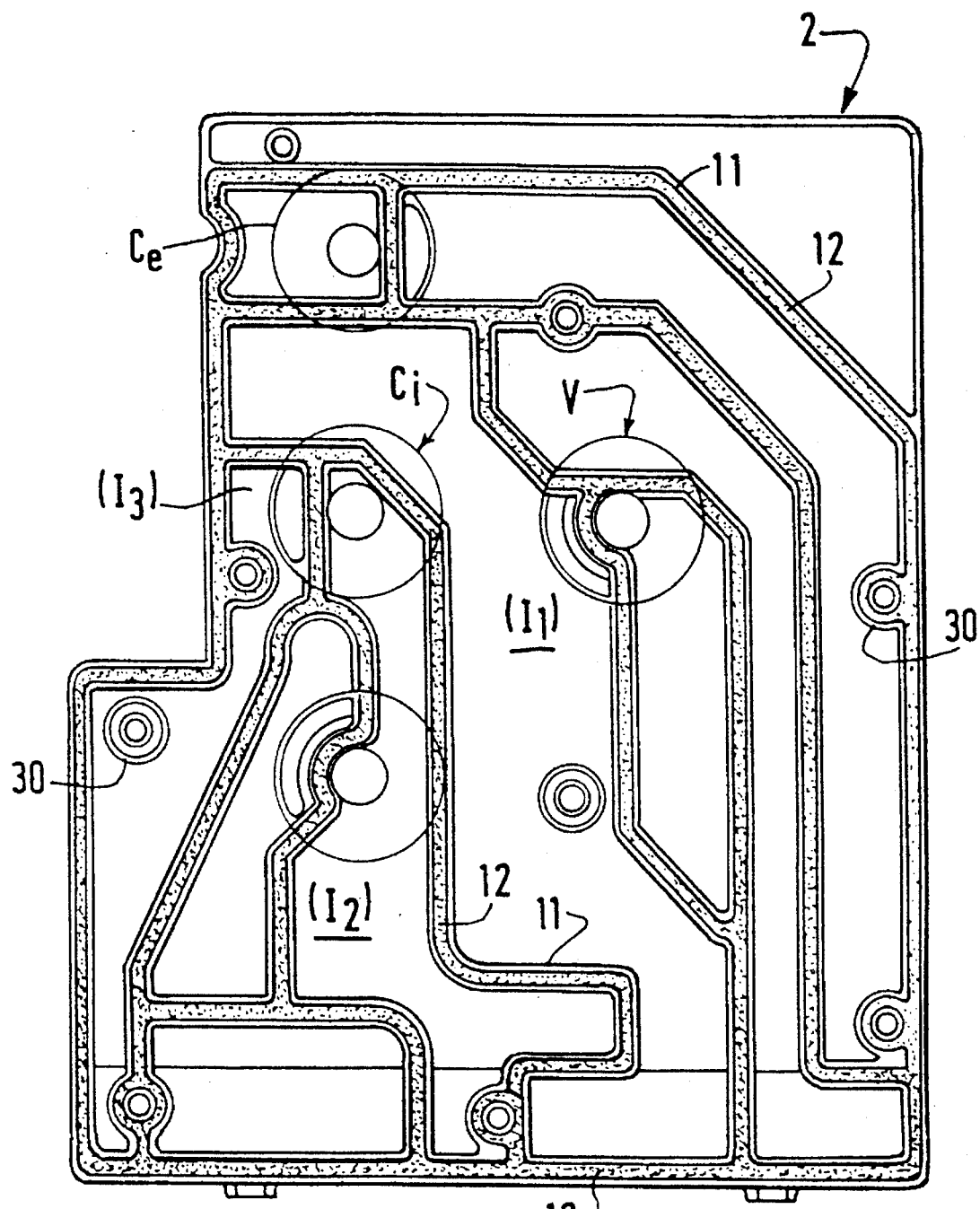
FIGS. 2 and 3 are plan views of the internal coacting surfaces of a cover and of a body of a subassembly according to the invention.

As shown in FIG. 2, the cover 2 comprises a network of grooves 11, also of trapezoidal profile but becoming thinner inwardly, corresponding exactly to the network of ribs 10 of the body 1. The bottom of the grooves 11 is totally occupied by sealing strip 12 injection molded into the grooves 11.

Figure 4:
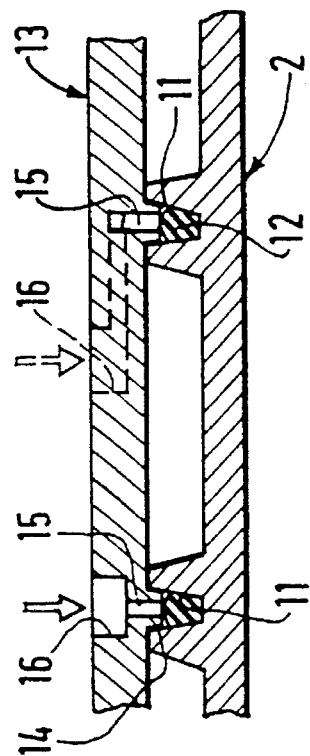
FIG. 4 is a schematic view showing the process of provision of the sealing strips of the cover of FIG. 2.

The process of production of the joints 12 is shown in FIG. 4 in which are shown the cover 2 and two grooves 11. In the plane defined by the external edges of the grooves 11 is applied a molding plate 13, for example of polymethylmethacrylate, whose active surface comprises short ribs 14 distributed according to the pattern of the grooves 11, which is to say analogous to the ribs 10 of the cover 1. At regular intervals in the ribs 14 open ejection channels 15 communicating, via a network of internal conduits in the plate 13, with openings 16 for the injection of elastomeric material. Thus, as shown in FIG. 4, upon positioning the molding plate 13 on the cover 2 with its ribs 14 received in the grooves 11, there is injected through the openings 16 a liquid silicone composition, typically at ambient temperature, which distributes itself via the ejection orifices 15 within the grooves 11 to fill totally the space delimited in this latter by the injection ribs 14. This operation is followed by a heating phase adapted to activate the polymerization of the silicone composition. Upon withdrawing the mold plate 13, the strips 14 will be solidified and will adhere to the grooves 11 that they partially fill to coact to provide fluidtightness, in the configuration of the mounting of the subassembly block B, with the external ends of the ribs 10 of the body 1 during mounting of the cover 2 on the body 1.

The body 1 and the cover 2 are preferably made of injection molded thermoplastic material, for example of polysulfone permitting disinfection and sterilization treatments by autoclaving. The internal surface of the body 1 is arranged to permit the suspended attachment of the casing of the bellows S and of the adsorbent body A, preferably of the type described in FR-A-2701400, in the name of the applicant. The openings 3–5 for connection to the gas circuits are disposed on one side of the body 1 and the connections to the active members and to the detector circuits are assembled on a lateral side of the body 1 (the lower side in FIG. 3) to permit removably plugging in the subassembly block B within the frame of the anesthetic apparatus. In particular, as shown in FIG. 3, the body 1 defines preferably a circuit portion for the pressurization of the bellows S between a compressed air inlet 20 and an opening 21 for communication with the chamber of the bellows S. The non-return valves $C_i$ and $C_e$ are preferably disposed, so that they will be visible, on the cover 2. The cover 2 and the body 1 are typically assembled by screws received in collars such as 30 which also form crosspieces for rigidification of the assembled subassembly block.

Although the invention has been described in relation to particular embodiments, it is not thereby limited but is on the contrary susceptible to modifications and variations which will be apparent to one skilled in the art.

We claim:

1. A gas circuit manifold comprising:

a body having a first face with a pattern of outwardly extending ribs delimiting at least two gas conduit portions;

a cover having a first face with a pattern of grooves mating with the pattern of ribs of the body; and a continuous seal deposit arranged in the grooves to cooperate in sealing contact engagement with the ribs when the body and the cover are assembled together, said seal deposit comprising injection molded elastomeric sealing material.

2. The gas circuit manifold of claim 1, wherein the sealing material is a silicone.

3. The gas circuit manifold of claim 1, wherein the body is formed of a molded thermoplastic material.

4. The gas circuit manifold of claim 1, wherein the grooves are formed in raised portions of the first face of the cover.

5. The gas circuit manifold of claim 1, for use in an anaesthetic apparatus, wherein the body has a second face comprising means for connection to ventilating bellows.

6. The gas circuit manifold of claim 1, for use in an anaesthetic apparatus, wherein the body has a second face comprising means for mounting an adsorbent cartridge.

7. The gas circuit manifold of claim 1, wherein the grooves have a substantially trapezoidal cross-section converging outwardly.

8. The gas circuit manifold of claim 7, wherein the ribs have a substantially trapezoidal cross-section diverging outwardly.

9. The gas circuit manifold of claim 8, wherein the body is formed of a molded thermoplastic material.

\* \* \* \* \*